United States Patent [19]

Chang et al.

[11] Patent Number: 4,661,624

[45] Date of Patent: Apr. 28, 1987

[54] PROCESS FOR THE PRODUCTION OF METHYL FORMATE

[76] Inventors: Tsuan Y. Chang, 1038 Wood Park Dr., Baldwin, N.Y. 11510; Neil Yeoman, 1723 Alexis Rd., Merrick, N.Y. 11566; Ronald F. Cascone, 40 W. 24th St., New York, N.Y. 10010

[21] Appl. No.: 639,772

[22] Filed: Aug. 13, 1984

[51] Int. Cl.[4] .............................................. C07C 67/36
[52] U.S. Cl. .................................................... 560/232
[58] Field of Search ......................................... 560/232

[56] References Cited

U.S. PATENT DOCUMENTS 3,716,619  2/1973  Lynn et al. ........................... 560/232

FOREIGN PATENT DOCUMENTS 1147214  4/1963  Fed. Rep. of Germany ...... 560/232
1442631  5/1966  France ................................. 560/232
1084549  9/1967  United Kingdom ................ 560/232

Primary Examiner—Werren B. Lone
Attorney, Agent, or Firm—Harold N. Wells

[57] ABSTRACT

A process for the production of alkyl formates such as methyl formate from the reaction of a carbon monoxide containing gas and an alkyl alcohol, such as methanol, is disclosed. The process features low conversions of alkyl alcohol to alkyl formate, high catalyst concentrations, higher reaction zone temperatures, improved process thermal efficiencies, and reduced apparatus requirements.

11 Claims, 1 Drawing Figure

PROCESS FOR THE PRODUCTION OF METHYL FORMATE

BACKGROUND OF THE INVENTION

1. Field of the Invention

The present invention relates to a process for the production of alkyl formates from the reaction of a carbon monoxide containing gas and an alkyl alcohol and, more particularly, to an improved process for the production of methyl formate from the reaction of carbon monoxide and methanol in the presence of high concentrations of a homogeneous alkali metal methoxide catalyst at elevated pressures and relatively high temperatures.

Carbon monoxide is a common constituent of fuel gases, including synthesis gas (syngas), water gas, steamhydrocarbon reforming gases, blast furnace gas and the like. Removing and recovering the carbon monoxide content from these fuel gases, either as a step in purifying the fuel gas or for providing a source of carbon monoxide as a raw material, is well known in the art.

2. Description of the Prior Art

The industrial production of the alkyl formates, particularly methyl formate, has encountered a number of difficulties which have frustrated the development of a successful process. For example, the reaction synthesizing methyl formate from CO and methanol is quite exothermic, thereby creating substantial heat removal problems. Additionally, the traditional catalysts of choice, i.e., the alkali metal methoxides, have a substantial solubility in the alkyl alcohols, e.g., methanol, but a very low solubility in the desired alkyl formate, e.g., methyl formate, products of the reaction; consequently, a solid catalyst precipitate may form during the process and create substantial process impediments, e.g., clogging the pipes of the apparatus and frustrating effective heat transfer therein. Also, when using the low catalyst concentrations of the prior art, the reaction will be slow and require long residence times, and thus substantial equipment costs.

U.S. Pat. No. 3,716,619 discloses a process for recovering CO from blast furnace gas by compressing the gas and then reacting CO with a lower alcohol to form an alkyl formate. The formate is separated from the fuel gas and the CO is regenerated by decomposition of the formate. Such a process requires a low concentration of sodium methoxide as catalyst, and the liquid phase reaction is carried out at relatively modest temperatures, thereby frustrating an economical operation.

U.S. Pat. No. 4,216,336 discloses a process for the production of methyl formate whereby a gas containing CO is reacted at 70° to 110° C. and 20 to 110 bars in a reaction zone with a liquid mixture containing methanol and a catalyst. The process is further characterized by the recycle liquid reaction mixture being sucked in and dispersed in a certain mechanical manner in the current of gas introduced into the reaction zone. The amounts of sodium methoxide catalyst suitable for the process and the resulting reaction rates, however, are still relatively minimal.

German Patent Specification No. 926,785 also utilizes a small amount of catalyst so as to prevent precipitation thereof, but the resulting yields are uneconomic and the process also requires mechanical stirring at the extremely high pressures involved.

German Patent Specification No. 1,046,602 utilizes a two stage reaction zone for the contacting of carbon monoxide with methanol. However, the process requires that the CO pressure, the temperature of the cooling water, the reactant purity and other parameters be constantly monitored.

German Patent Specification No. 1,147,214 also contacts CO with methanol, but is an extremely cumbersome process.

Applicants have discovered a novel, improved process of synthesizing alkyl formates, particularly methyl formate, in a liquid phase reaction involving contacting an alkyl alcohol, e.g., methanol, with a CO containing gas, e.g., syngas, present at relatively high partial pressures in the presence of a homogeneous alkali metal methoxide, e.g., sodium methoxide, catalyst. The synthesis is conducted in, preferably, a two stage reaction zone in a low conversion process in which the CO containing gas is contacted in each zone with a fresh recycled alcohol stream containing high catalyst concentrations, under reaction zone conditions favoring high reaction rates, e.g., a high temperature reaction zone.

Accordingly, it is an object of the present invention to provide an improved process for the production of alkyl formates, particularly methyl formate, from a CO containing pressurized gas, e.g., a coal or heavy residual oil syngas, involving minimal capital expense, high catalyst concentrations and reaction rates and minimal heat requirements.

It is another object of the invention to provide an industrially acceptable process involving low per pass conversions of an alkyl alcohol into the corresponding alkyl formate.

It is still another object of this invention to develop a process having excellent conversions of carbon monoxide into methyl formate.

SUMMARY

In accordance with the aforementioned objects, a novel process for the production of alkyl formates, preferably methyl formate, has been discovered. The process comprises preparing a suitable CO-containing gas stream, e.g., a purified, pressurized coal or residual oil gasification stream, such as the product of a Texaco gasifier; reacting the CO in the stream with a lower alkyl alcohol stream, preferably a recycled methanol stream, in a, preferably first reaction zone, preferably a reactor adapted for substantial amounts of internal liquid circulation. The reaction occurs at a temperature of about 70° to 130° C., preferably about 90° to 120° C., and a CO partial pressure of about 70 to 1000 psia in the presence of a concentrated amount, e.g., about 1.0 to 8.0 mole %, preferably about 2.0 to 6.0 mole % of homogeneous alkali metal methoxide catalyst, e.g., sodium methoxide, present in the alcohol stream with the conversion of alkyl alcohol to alkyl formate being kept to low relative amounts, e.g., formate concentrations of 2 to 20 mole %, so as to permit the usage of higher concentrated amounts of homogeneous catalyst in the alcohol stream; preferably further reacting the CO containing stream with a fresh alkyl alcohol containing concentrated catalyst stream in a second reaction zone, e.g., a countercurrent contacting column, to convert a substantial amount of still unreacted CO into alkyl formate; passing the effluents from the reaction zone or zones in separate streams to a distillation zone; separating the formed alkyl formate, e.g., methyl formate, from the alkyl alcohol, e.g., methanol, in the distillation zone; and recycling the alkyl alcohol containing concentrated catalyst stream, preferably replenished with fresh alcohol, if required, in separate streams to the first and, preferably, also the second reaction zones, and repeating the above sequence of steps.

DETAILED DESCRIPTION OF THE INVENTION

Figure 1:
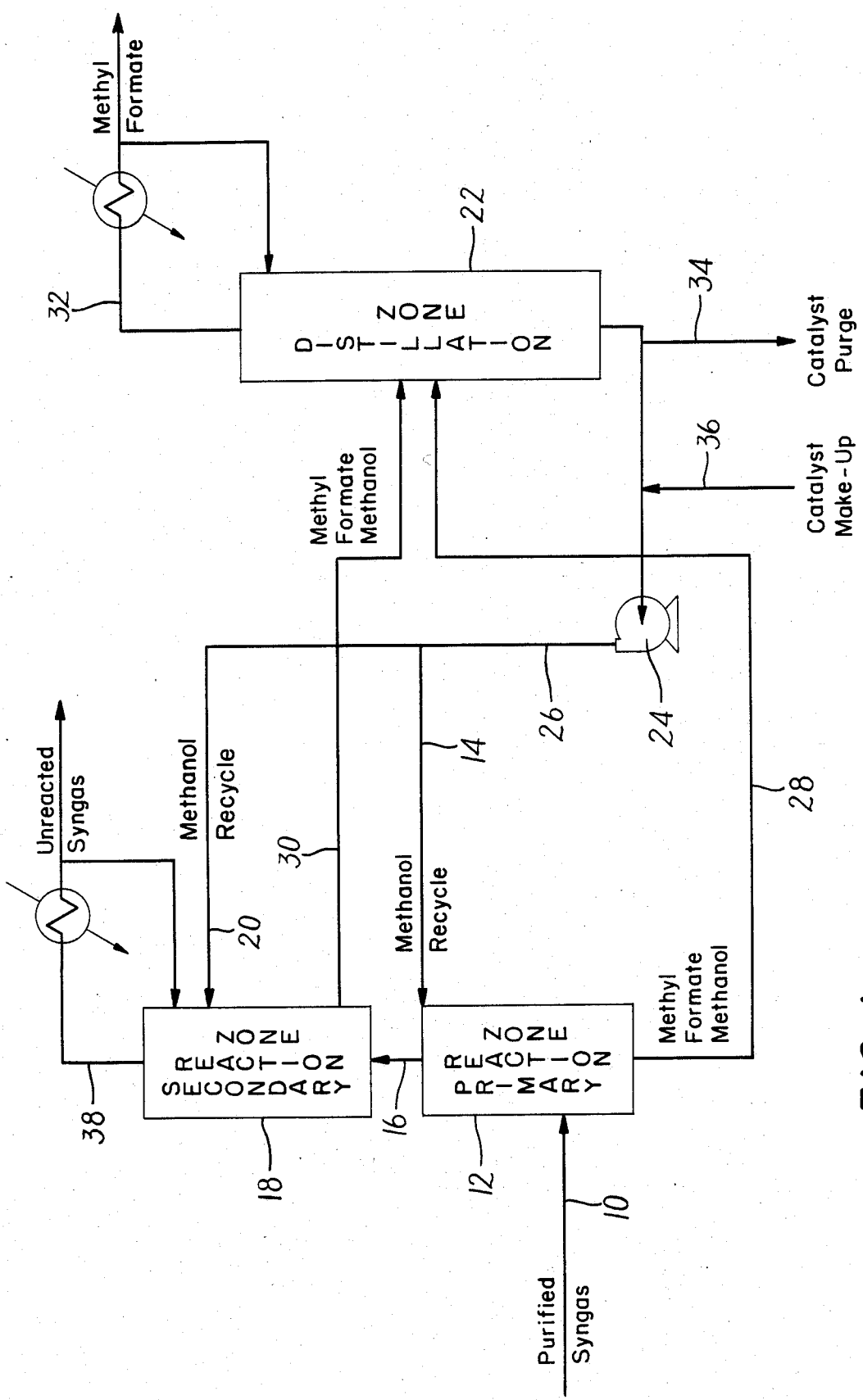

In the broadest embodiment the invention comprises a process for the synthesizing of a lower alkyl formate, preferably methyl formate, in a liquid phase reaction by reacting a lower alkyl alcohol, preferably methanol, with a CO containing gas, e.g., a coal or heavy residual oil gasification "syngas", at relatively high CO partial pressures and moderate temperatures. The reaction is catalyzed by the presence of relatively high concentrations of an effective homogeneous catalyst, preferably a homogeneous alkali metal methoxide, most preferably sodium methoxide, in the alcohol. The resulting highly exothermic reaction is limited in conversion by chemical reaction equilibrium, with the unreacted alcohol being separated from the alkyl formate reaction product by a suitable distillation. The unreacted alcohol, together with a fresh amount, if required, for replenishment, is recycled in two streams to the corresponding two synthesis, reaction zones, if two reaction zones are employed, as preferred, although in the broadest embodiment only one is essential.

Referring to FIG. 1, which sets forth a schematic outline of the preferred embodiment of the invention, a suitably purified syngas stream, preferably produced from a coal or heavy residual oil gasification process, or the like, and maintained at elevated pressures, e.g., about 900 psia and about 5° C. to ambient temperature, e.g., about 25° C., is passed through line 10 into the primary reaction zone 12. Although a wide variety of purified CO containing gases are suitable, it is convenient, for purposes of illustration, to use a syngas containing about 59 mole % CO, about 40% $H_2$, and about 1% of inerts such as methane, nitrogen, argon and the like, with the concentration of each of the undesirable gases, e.g., $H_2S$, COS, $CO_2$, and $H_2O$ being kept to about one part per million or less. Reaction zone 12 contains, in addition to the entering CO containing gas stream, a sodium methoxide ($NaOCH_3$) catalyst in concentrations of about 1.0 to 8.0 mole %, preferably 2.0 to 6.0 mole %, dissolved in a methanol recycle stream which enters the primary reaction zone through line 14 from the distillation zone.

It is preferred that a two stage reaction zone be employed for the process of the invention, with the primary i.e., first, reaction zone being equipped with a draft tube, a mechanical agitator, or another suitable means for achieving a high internal liquid circulation. It is also preferred that the primary reaction zone be operated at relatively high temperatures, i.e., about 90° to 110° C., for the reaction to proceed at a high reaction rate, thereby substantially minimizing the required reactor volume, along with the attendant capital construction costs. A gas stream containing the unreacted CO exits the primary reaction zone 12 through line 16 and, in the usual and preferred embodiment where more CO conversion is desired, passes into secondary reaction zone 18, which preferably consists of a suitable column reactor containing bubble-cap trays or other contacting devices, and in which the CO containing gas flows countercurrent to a second, smaller recycled methanol stream 20 from the distillation zone entering at the top of the column. The column reaction zone 18 operates at relatively low temperatures, e.g., about 70° to 90° C. in the preferred case, as compared with the hotter primary reaction zone, in order to achieve superior equilibrium conversions of CO. An essential element of the process is that the synthesis of the alkyl formate be carried out under low conversion conditions, that is, the fraction of methanol present converted to methyl formate per pass is kept low, i.e., about 2 to 20 mole %. Returning to the figure, the two recycle methanol streams 14 and 20 both originate from the bottom of the distillation zone 22 and are pumped by pump 24 through line 26 back to the primary and secondary reaction zones. Also in the case of multiple reaction zones, the two effluent streams 28 and 30 emanating from the primary and secondary reactors respectively, containing the product methyl formate, unreacted methanol and homogeneous catalyst pass into the distillation zone 22 in two separate effluent streams. As will be apparent to those skilled in the art, hydraulic turbines can be installed on the reactor effluent streams in large plants to recover power which, for example, can be used to provide power for pump 24, or the like. Such a system of routing and recycling the various streams between the reaction and the distillation zones is essential for most effective operation in the low conversion mode utilized for process operation. The precise distribution of the two recycled methanol streams back to the primary and secondary reaction zones, as well as their temperatures must be properly controlled for effective operation and methanol conversion. Since only a relatively small amount of the total CO conversion will occur in the secondary reaction zone, a relatively small percentage e.g., about 10 to 30 wt. % of the total recycled alcohol, will be fed into the top of the reaction zone 18 through line 20. Preferably this methanol stream will have a temperature between about 60° to 80° C., most preferably about 70° C., when entering the reaction zone for optimum equilibrium conditions and methyl formate production in the top section of the reaction zone. As the methanol stream flows down column 18, which is equipped with bubble-cap trays or other contacting apparatus, countercurrent to the rising CO containing gas stream, its temperature will rise, but the partial pressure of CO in the gas phase it comes into contact with will also increase, thus creating an environment suitable for an efficient synthesis of methyl formate. Although not shown in the figure, suitable cooling units for the descending liquid stream can be provided on the trays and, if necessary, between the two sections of reaction zone 18 in order to maintain optimum operating temperatures in the second reaction zone.

A larger recycled methanol stream, typically ranging from about 70 to 90 wt. % of the recycled alcohol, is fed through line 14 into the primary reaction zone 12 where the bulk of the methyl formate is synthesized. The large recycle stream also controls the temperature of the reaction zone by absorbing the heat from the exothermic reaction to maintain the reactor at about 90° to 110° C., which is the preferred operating temperature. A suitable cooling unit can be provided if needed, for the recycle methanol in line 14 to maintain the temperature in reaction zone 12 at the desired value.

The two methanol-methyl formate effluent streams 28 and 30 from the two reaction zones are each separately passed to the middle section of distillation zone 22 for the separation of the methyl formate fraction, ranging from about 80 to 90 mole % methyl formate, which leaves through the top of the column in line 32, while an essentially pure methanol fraction leaves through the bottom in line 26 for recycle to the reaction zones. In order to maintain the desired amount of catalytic activity, a stream 34 of the recycle methanol containing catalyst is purged from line 26 at a point before pump 24, while concurrently stream 36 containing fresh catalyst is added to line 26 downstream from the purging point. In both the reaction zone and the distillation zone sections, a conventional overhead system (not shown) such as one comprising a water-cooled condensor followed by a refrigerant-cooled condensor can be provided so as to minimize the loss of methyl formate and methanol in the unreacted gas and the vent gas streams 38 and 32 leaving the second reaction zone and distillation zone systems, respectively.

The products passing from the top of the distillation zone in line 32 include carbon monoxide, hydrogen, methyl formate vapor, and methanol vapor.

The methanol, or other alkyl alcohol suitable for use in the process of the present invention, should range from chemically pure down to technical grade quality. As in the case of carbon monoxide, the methanol should contain the smallest possible amount of water, for example, less than about 100 ppm of water.

The molar ratio of carbon monoxide to methanol, or other chosen alkyl alcohol, in the process of the invention is preferably kept between about 0.10 to 0.60, most preferably, from 0.15 to 0.45. As mentioned above, an essential parameter of the process is the relatively low conversion per pass of the alkyl alcohol, e.g., methanol, to the alkyl formate, e.g., methyl formate, in the reaction zone. When the concentration of the formed product methyl formate in methanol is low this permits higher concentrations of the homogeneous catalyst to be used without fear of catalyst precipitation, thereby resulting in a higher reaction rate and, consequently, a smaller reactor cost. Such an increase in catalyst concentration is possible because the preferred catalysts such as sodium methoxide have a substantial solubility in methanol, but a very low solubility in methyl formate. Thus a lower concentration of methyl formate product in the methanol stream permits the use of higher concentrations of catalyst without the danger of harmful precipitation and the harmful results accompanying this phenomenon. The second major benefit of lower conversion operation is the ability to operate the reaction zone at higher temperatures for a given CO partial pressure present, which enables a higher reaction rate to be achieved in the reaction zone. An additional benefit of such a process is the very favorable heat economies created by such a process. The heat liberated in the alkyl formate synthesis is primarily absorbed by the effluent stream passing from the primary reaction zone, which is operated at temperatures of 90° C. or higher. The sensible heat present in the effluent is conveniently utilized in the distillation zone, thereby minimizing the reboiler duty required for the product separation. A portion of the methyl formate-methanol mixture is flashed in the column, and this flash vapor, together with the vapor generated in the reboiler, is sufficient to meet the requirements for stripping the methyl formate from the methanol and rectification of the methyl formate. It is also likely that the column bottoms of the distillation zone can be recycled to the primary reactor with little or no cooling requirement, thus further contributing towards high thermal efficiency for the process.

EXAMPLE 1

Utilizing the process outline set forth in FIG. 1, 16,170 moles per hour of purified syngas from a Texaco coal gasification plant are fed through line 10 to the primary reaction zone 12. The syngas comprises approximately 59 mole % CO, 40 mole % $H_2$ and 1 mole % of inerts such as $CH_4$, $N_2$ and Ar. 58,700 moles per hour of essentially pure metahanol, containing 4.0 mole % of dissolved sodium methoxide catalyst, is recycled from the distillation zone 22 to the first, or primary, reactor. In the reactor, which operates at about 900 psia and 100° C., the CO and the methanol react and form methyl formate. The reactor 12 features a draft-tube design, in which the feed gas is sparged into a centrally located vertical tube. The gas mixes into and lifts the liquid reaction mixture into the space above the top of the tube, where the liquid separates from the gas. The liquid then falls through an annular space existing between the tube and the reactor shell and re-enters the bottom end of the central tube. The unreacted gas passes out of the reactor and goes to the second reactor. By such a technique a very high internal liquid circulation is maintained. The reactor effluent, containing a mixture of methanol and about 11 mole % of methyl formate product and some dissolved gases returns to the middle of distillation column 22, which operates at about 18 psia and 40° C. at the top and about 22 psia and 75° C. at the bottom. The reactor effluent flashes upon entering the distillation column, and the flashed vapor reduces the heat duty supplied by a steam-heated reboiler at the bottom of the column. The distillation column also processes the liquid effluent stream from the second, or column, reactor.

The unreacted gas from the primary reactor, comprising about 9,710 moles per hour and containing approximately 31.3 mole % CO, 66.7 mole % $H_2$ and 2.0 mole % of inerts, having had about 68% of the CO content removed in the primary reaction zone, leaves and enters into the second reaction zone 18. Reaction zone 18 forms a vertical column equipped with bubble-cap trays. The reacting liquid alcohol mixture passes downward in the column, countercurrent to the upward flowing unreacted CO containing gas which has exited the primary reaction zone. 17,000 moles per hour of methanol is also recycled from distillation zone 22 to the top of the column reactor through line 20. The mixture enters the reactor at about 75° C. and flows down the column reactor in a countercurrent manner to the gas stream rising from the first reaction zone. Due to the presence of cooling coils on the bubble-cap trays, the temperature rise of the liquid reaction mixture can be controlled, and the liquid effluent leaves the column reactor at about 90° C. By careful control of the operating conditions, an additional 20% of the CO in the syngas is captured in the reactor, boosting the overall CO conversion in the two reactors to about 88%. The reactor effluent from the second reaction zone 18, containing about 1,900 moles per hour of methyl formate and 15,100 moles per hour of methanol, is returned to the middle of distillation zone 22 through line 30.

The distillation column separates the two reactor effluent streams into a top product stream containing about 8,360 moles/hr of methyl formate and 930 moles per hour of methanol. The overhead product and reflux of the column are condensed and separated in a knock-out drum, while the dissolved gases are vented from the system. The bottom product of the distillation column comprises essentially pure methanol, and is recycled by pump 24 to the primary reaction zone 12 and the secondary reaction zone 18. About 9,290 moles per hour of make-up methanol are added to the bottom of the column.

The unreacted gas leaving the second reaction zone 18 passes through a condensing system from which the condensed methanol and methyl formate are returned to the reactor. The gas, about 7,810 moles per hour leaving the condensing system, contains about 14.6 mole % CO, 82.9 mole % $H_2$ and 2.5 mole % inerts. It can be either used as fuel or upgraded to a hydrogen purity suitable for various industrial uses.

To summarize, a total of 8,360 moles per hour of methyl formate is synthesized in the process, of which 6,460 is formed in the primary reactor and 1,900 in the secondary reactor.

EXAMPLE II 10,000 moles per hour of a purified syngas from the partial oxidation of residual oil, that is, hydrocarbons unsuitable for use as fuel oil, are fed through line 10 to the primary reaction zone 12, which is a conventional mechanically agitated, back-mixed reactor. The syngas is comprised of approximately 49% CO, 49% $H_2$ and 2% inerts such as methane, nitrogen and argon, and is free of the undesirable gases such as $H_2S$, COS, $CO_2$ and water vapor. 22,000 moles per hour of essentially pure methanol, containing 4.0 mole % of dissolved sodium methoxide catalyst, is recycled from the distillation zone 22 to the primary reactor. In the reactor, which operates at 800 psia and 90° C., the CO in the syngas reacts with the methanol to form methyl formate. The reactor effluent, containing a mixture of 19,800 moles per hour of methanol, 2,200 moles per hour of methyl formate and small amounts of some dissolved gases, is returned to the middle of the distillation column 22. The distillation column is maintained at about 18 psia and 40° C. at the top and about 22 psia and 75° C. at the bottom. The unreacted gas leaving the primary reactor, about 7,800 moles per hour, contains 34.6% CO, 62.8% $H_2$ and 2.6% inerts. About 45% of the CO in the feed gas is converted to methyl formate in the first reactor. The unreacted gas enters the second, or column reactor 18 which is a bubble-cap tray column. 8,000 moles per hour of methanol are recycled through line 20 from distillation zone 22 to the top of the second reactor. The second reactor is operated so as to capture about 6% of the CO in the feed gas and the reactor effluent is returned to the middle of distillation column 22. Since the amount of CO capture in the second reactor is small and the recycle methanol stream is relatively large, the temperature rise of the reacting mixture in descending through the column will be moderate, e.g., the recycle methanol enters the column at about 75° C. and the reactor effluent leaves at about 90° C. Thus, adiabatic operation of the second reactor is feasible and no cooling water is needed for the coils on the trays.

The combined effluents from the first and the second reactors are separated in the distillation column into a top product containing 2,500 moles per hour of methyl formate and 280 moles per hour of methanol, and a bottom product of 27,220 moles per hour of essentially pure methanol. The bottoms stream, after the addition of about 2,780 moles per hour of make-up methanol, is recycled back to the two reactors in two separate streams as described earlier.

The total capture of CO by the two reactors is approximately 51% of the CO in the feed gas. The unreacted gas leaving the second reactor, about 7,500 moles per hour, contains about 65.3% $H_2$, 32.0% CO and 2.7% inerts. It should be noted that the $H_2$/CO ratio in this unreacted gas is about 2.04, which makes it an excellent feedstock for methanol synthesis.

EXAMPLE III

Utilizing the same apparatus as set forth in Example I, except that only a primary reactor is employed, 16,170 moles per hour of purified syngas from a Texaco coal gasification plant are fed through line 10 to the primary reaction zone 12. The syngas comprises approximately 59 mole % CO, 40 mole % $H_2$ and 1 mole % of inerts such as $CH_4$, $N_2$ and Ar. 58,700 moles per hour of essentially pure methanol, containing 4.0 mole % of dissolved sodium methoxide catalyst, is recycled from the distillation zone 22 to the reactor 12. In the reactor, which operates at about 900 psia and 100° C., the CO and the methanol react and form methyl formate. The reactor 12 features a draft-tube design, as so described in Example I. The reactor effluent, containing a mixture of methanol and about 11 mole % of methyl formate product and some dissolved gases, returns to the middle of distillation column 22, which operates at about 18 psia and 40° C. at the top and about 22 psia and 75° C. at the bottom. The reactor effluent flashes upon entering the distillation column, and the flashed vapor reduces the heat duty supplied by a steam heated reboiler at the bottom of the column.

The unreacted gas from the reactor, comprising about 9,710 moles per hour and containing approximately 31.3 mole % CO, 66.7 mole % $H_2$ and 2.0 mole % of inerts, having had about 68% of the CO content removed in the primary reaction zone, leaves and passes through a condensing system from which the condensed methanol and methyl formate are returned to the reactor. This unreacted gas has a $H_2$/CO ratio of 2.13 and is an excellent feedstock for methanol synthesis.

The distillation column separates the reactor effluent stream into a top product stream containing about 6,460 moles per hour of methyl formate and 720 moles per hour of methanol. The overhead product and reflux of the column are condensed and separated in a knock-out drum, while the dissolved gases are vented from the system. The bottom product of the distillation column comprises essentially pure methanol, and is recycled by pump 24 to the primary reaction zone 12. About 7,180 moles per hour of make-up methanol are added to the bottom of the column.

We claim:
1. A thermally efficient process for the production of alkyl formates comprising:
    preparing a CO containing gas stream having a concentration of $H_2S$, COS, $CO_2$ and $H_2O$ of about one part per million of or less;
    reacting the CO in the gas stream with a lower alkyl alcohol in a reaction zone at a temperature from about 70° to 130° C. and a CO partial pressure of about 70 to 1000 psia, in the presence of a homogeneous sodium alkoxide catalyst to from an alkyl formate; said catalyst having a concentration in the alcohol which ranges from about 1.0–8.0 mole % of alcohol and the conversion of alkyl alcohol to alkyl formate ranging from about 2-10 mole % of the alcohol present in the reaction zone; the process being substantially free of catalyst precipitation;

withdrawing an effluent stream from said reaction zone containing alkyl formate and alkyl alcohol and separating the formed alkyl formate from the alkyl alcohol in a distillation zone;

recycling the alkyl alcohol containing concentrated catalyst to the reaction zone.

2. A process as claimed in claim 1 wherein the process comprises further reacting the CO containing gas stream after the reaction of claim 1 with a fresh alkyl alcohol containing about 1.0-8.0 mol % of catalyst in a second reaction zone to convert a substantial amount of unreacted CO into alkyl formate;

withdrawing an effluent stream from said second reaction zone containing alkyl formate and alkyl alcohol and separating the formed alkyl formate from the alkyl alcohol in a distillation zone;

further recycling the alkyl alcohol containing catalyst to the second reaction zone;

3. A process as claimed in claim 2 wherein the effluents from the first and second reaction zone are passed in separate streams to a distillation zone.

4. A process as claimed in claim 1 wherein the CO containing stream is a purified coal or heavy residual oil gasification stream.

5. A process as claimed in claim 2 wherein the second reaction zone is a column for countercurrent contacting of the alkyl alcohol and CO containing gas streams.

6. A process as claimed in claim 2 wherein the alkyl alcohol containing catalyst streams entering the first and second reaction zones are recycle streams passed from the distillation zone.

7. A process as claimed in claim 1 wherein the recycled alkyl alcohol stream to the reaction zone is maintained at a temperature of about 60° to 80° C.

8. A process as claimed in claim 2 wherein the heat requirement of the distillation zone is partially provided by the effluent streams from the first and second reaction zones.

9. A process as claimed in claim 2 wherein the recycled alkyl alcohol stream to the second reaction zone is maintained at a temperature of about 60°-80° C.

10. A process as claimed in claim 1 wherein the heat requirement of the distillation zone is partially provided by the effluent stream from the reaction zone.

11. A process as claimed in claim 1 wherein the CO containing stream is a syngas stream.

* * * * *